(12) United States Patent
Brans et al.

(10) Patent No.: US 8,339,608 B2
(45) Date of Patent: Dec. 25, 2012

(54) METHOD FOR DETECTING REDISPERSION OF BEADS

(75) Inventors: Harold Johannes Antonius Brans, Eindhoven (NL); Albert Hendrik Jan Immink, Eindhoven (NL); Hendrik Sibolt Van Damme, Eindhoven (NL); Mara Johanna Jacoba Sijbers, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 191 days.

(21) Appl. No.: 12/740,148

(22) PCT Filed: Oct. 30, 2008

(86) PCT No.: PCT/IB2008/054514
§ 371 (c)(1),
(2), (4) Date: Aug. 17, 2010

(87) PCT Pub. No.: WO2009/060358
PCT Pub. Date: May 14, 2009

(65) Prior Publication Data
US 2010/0309472 A1 Dec. 9, 2010

(30) Foreign Application Priority Data
Nov. 5, 2007 (EP) .................................. 07120001

(51) Int. Cl.
*G01N 21/55* (2006.01)
(52) U.S. Cl. ....................................................... 356/445
(58) Field of Classification Search .................. None
See application file for complete search history.

(56) References Cited

U.S. PATENT DOCUMENTS

| 4,849,340 | A | 7/1989 | Oberhardt |
| 5,637,458 | A | 6/1997 | Frankel et al. |
| 7,361,472 | B2 * | 4/2008 | Yguerabide et al. ........... 435/7.1 |
| 2003/0215825 | A1 | 11/2003 | Tong |
| 2005/0014179 | A1 | 1/2005 | Karlsson |
| 2005/0048599 | A1 | 3/2005 | Goldberg et al. |
| 2006/0134713 | A1 | 6/2006 | Rylatt et al. |
| 2006/0146333 | A1 * | 7/2006 | Hakamata et al. ............ 356/445 |
| 2007/0031283 | A1 | 2/2007 | Davis et al. |
| 2007/0153284 | A1 | 7/2007 | Glazier et al. |

FOREIGN PATENT DOCUMENTS

| EP | 1801594 A1 | 6/2007 |
| WO | 2004031743 A1 | 4/2004 |
| WO | 2005010542 A2 | 2/2005 |
| WO | 2005010543 A1 | 2/2005 |
| WO | 2008142492 A1 | 11/2008 |
| WO | 2009016533 A1 | 2/2009 |

OTHER PUBLICATIONS

Bruckl et al: "Magnetic Particles As Markers and Carriers of Biomolecules"; IEEE Proceedings in Nanobiotechnology, vol. 152, Issue 1, Feb. 2005, pp. 41-46.

* cited by examiner

*Primary Examiner* — Tu Nguyen

(57) ABSTRACT

A method of detecting redispersion of particles into a solution using for example FTIR. The method including providing a sensor surface with dry particles; illuminating the sensor surface with light along a first optical path and detecting the light reflected by the sensor surface; providing a liquid to a volume in contact with the sensor surface; and detecting the reflected light while the dry particles redisperse into the liquid. The angle between the first optical path and the sensor surface fulfils the condition of total internal reflection. Further, an FTIR cartridge may be provided for use in said method. The cartridge including a sensor surface accessible for FTIR detection including at least one binding area wherein label particles are situated.

11 Claims, 2 Drawing Sheets

METHOD FOR DETECTING REDISPERSION OF BEADS

FIELD OF THE INVENTION

The invention relates to a method of detecting redispersion of beads and to a cartridge for use in said method.

BACKGROUND OF THE INVENTION

Biosensing, i.e. the determination of the amount of a specific molecule within an analyte, is receiving increasing interest. Usually the amount of analyte and, in particular, of the molecules of interest is extremely small. Therefore, label particles are used in order to visualize these molecules. For example, WO 2005/010543 A1 and WO 2005/010542 A2 describe biosensors based on the magnetic detection of superparamagnetic beads present at a sensor surface. Only, if the specific molecules of interest are present, the label beads bind to said sensor surface. Thus, the amount of bound label beads is correlated with the amount of specific molecules in the analyte. These label particles or beads may be supplied in solution or in dry form. In the latter case the beads in dry form are dispersed or redispersed in a liquid which comprises the analyte to be bound not until being in the biosensor. In the contrary beads provided in a solution are already dispersed when introduced into the biosensor.

SUMMARY OF THE INVENTION

It is an object of the present invention to provide a method of reliable operation of a biosensor. It is a further object of the present invention to provide a cartridge for use in said method.

The present invention is based on the idea to use Frustrated Total Internal Reflection (FTIR) to measure the redispersion of dry particles into solution.

Thus, the invention provides a method of detecting the redispersion of particles into a solution by means of FTIR comprising the following steps: providing a sensor surface with dry particles; illuminating the sensor surface with light along a first optical path and detecting the light reflected by the sensor surface; providing a liquid to a volume in contact with the sensor surface; and detecting the reflected light while the dry particles redisperse into the liquid. Therein, the angle between first optical path and sensor surface fulfils the condition of total internal reflection.

Accordingly, light illuminating the sensor surface along the first optical path is completely reflected at said sensor surface. However, if the index of refraction close to said sensor surface is inhomogeneous, e.g., due to the presence of said dry particles, the condition of total internal reflection is—at least partially—violated. This leads to scattering of light at this inhomogeneity and thus to a decrease in intensity of the reflected light, which is detected by an optical detector, e.g., a photo diode, a CCD camera or the like. Measuring the intensity of the reflected light allows for detection of said dry particles present at or very close to the sensor surface. Said signal may be monitored during the redispersion of the dry particles into the liquid: The more particles leave the sensor surface and redisperse, the less light is scattered at the sensor surface. Thus, more light is reflected and the increase in reflected intensity monitors the redispersion process. Obviously, the total amount of redispersed particles as well as the rate of the redispersion of the particles may be analyzed.

Preferably, the dry particles to be detected are label particles, in particular magnetic beads, which may be coated with specific binding or capture molecules. However, the redispersion of other particles may be measured as well.

The particles may also be used for alignment of an FTIR detector and/or the first optical path prior to redispersion of the particles.

The present invention also provides an FTIR cartridge for use in the method described above. Said cartridge comprises a sensor surface accessible for FTIR detection, said sensor surface comprising at least one binding area, wherein label particles are situated on said surface. In one embodiment, the label particles are situated on the at least one binding area of said surface.

These and other aspects of the invention will be apparent from and elucidated with reference to the embodiment(s) described hereinafter.

DETAILED DESCRIPTION OF EMBODIMENTS

Figure 1:
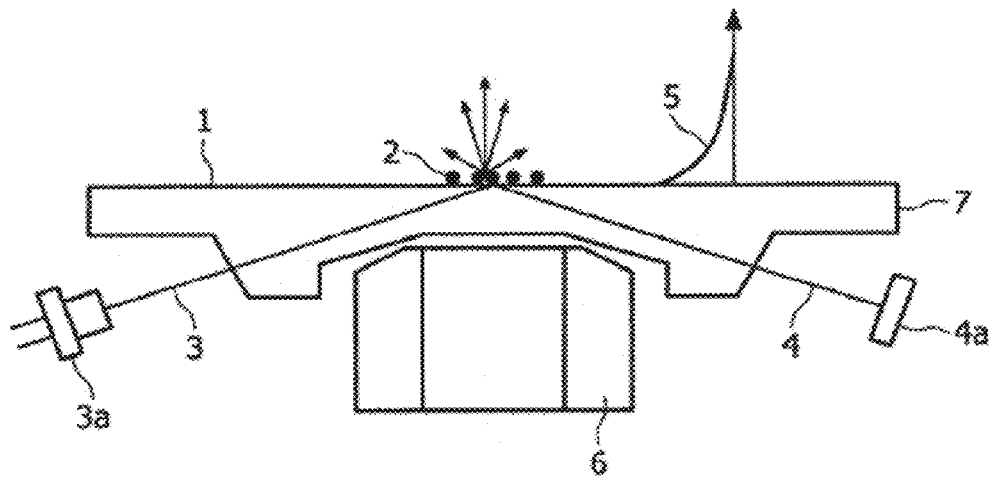
FIG. 1 schematically shows a side view of the principle of FTIR as an example of optical detection.

FIG. 1 schematically shows the functional principle of frustrated total internal reflection (FTIR) as an example of an optical detection method in connection with the present invention. Label particles 2 are provided on a sensor surface 1 of a cartridge 7. Sensor surface 1 is illuminated with a laser or LED 3a which is arranged in this example below the cartridge 7. The light depicted as a line representing a first optical path 3 is reflected at sensor surface 1 at the cartridge 7 and detected by a detector 4a, which may be, e.g., a photo diode or a CCD camera. Correspondingly, the detector 4a is arranged below the cartridge 7 opposed to the laser or LED 3a. The optical path 3 of incoming light is chosen such that the condition of total internal reflection is fulfilled, especially with respect to the angle of light impinging at the sensor surface 1, which is known in the art. In that case, an evanescent optical field 5 with a typical evanescent decay length of 100 nm to 1000 nm is generated. Thus, only if label particles 2 are sufficiently close to the sensor surface 1, light is scattered at these label particles 2 as indicated by the headed arrows having different directions above the label particles 2 and the evanescent field is disturbed leading to a decrease of reflected light intensity.

Once a liquid or sample liquid is supplied to the sensor surface 1 or to a (cartridge) volume adjacent to said sensor surface 1, label particles 2, which have been supplied in a dry form, redisperse into solution. The term redispersion means the dissolving or dispersion of beads in dry form into the sample liquid. The cartridge 7 therefore comprises a housing (not shown) to contain the solution. The liquid or sample liquid comprises an analyte to be detected later, which is not the object of this invention. Thus, the label particles 2 being solved within the sample liquid at the sensor surface 1 resulting in the label particles 2 not completely resting at the sensor surface 1, less light is scattered at the sensor surface 1 leading to an increased intensity in reflected light at detector 4a along the reflected optical path 4. This is true for assays in which the more bindings of label particles 2 occur to the assay the more analyte to be detected is present in the sample liquid. For example in inhibition assays it holds to the contrary true that the less bindings of label particles 2 occur to the assay the more analyte is present in the sample liquid. An assay may be provided at the cartridge 7 for binding of the analyte, the label particles 2 or further antigens, antibodies etc. to the sensor surface 1 in different known varieties. Nevertheless, the invention is not restricted to the use of an assay, but detection can take place also in the solution without binding to an assay. Once the label particles 2, which have preferably super-paramagnetic properties, are completely dispersed in the liquid sample, they may be accelerated towards sensor surface 1 using a magnet 6, which is arranged adjacent to the cartridge 7, in the example shown in FIG. 1 below the cartridge 7. The magnet 6 is a controllable electromagnet, which means the magnet is switched between different operating states, that allow the generation and deactivation of a magnetic field in the area of the sensor surface 1. The label particles 2 can bind to the sensor surface 1 in several manners in the case an assay is provided thereat. One binding manner is the binding of the label particles 2 to an antibody in the liquid sample which binds to molecule or analyte which in turn also binds to an antibody fixed at the assay. If the specific molecule or analyte to be detected is present in the liquid sample, the molecule or analyte is detected by the presence of the label particle 2 bound via the antibody to the molecule or analyte. With other words, the molecule or analyte is detected indirectly by a detection of the label particles 2. Several differing methods are known in the art using label particles 2 for optical detection.

Optical detection method of FTIR is now again used to measure the amount of bound particles 2. Thus, the same technique, namely FTIR, may be used to first measure the redispersion of label particles 2 into the liquid sample and then measure the binding properties of said label particles 2 due to the presence of one or more specific molecules or analytes.

Figure 2A:
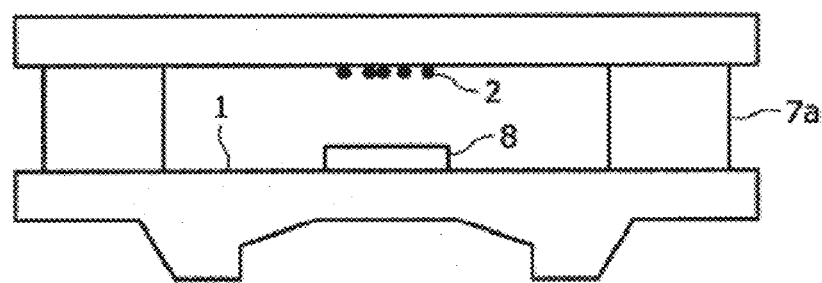
FIG. 2a schematically shows a side view of a FTIR cartridge.
Figure 2B:
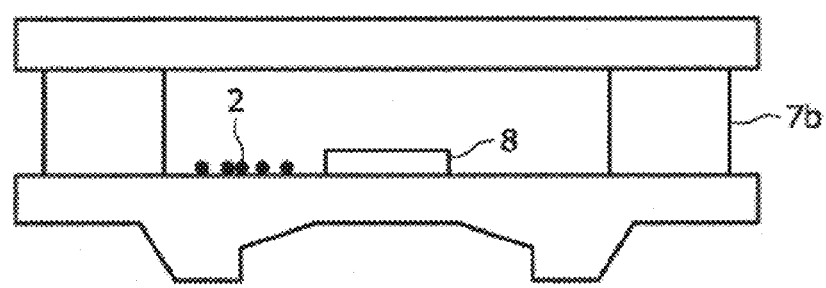
FIG. 2b schematically shows a side view of a preferred embodiment of an FTIR cartridge according to the present invention.

FIG. 2 schematically shows a common FTIR cartridge 7a (FIG. 2a) as well as a preferred embodiment of an FTIR cartridge 7b (FIG. 2b) according to an example of the present invention. Cartridges 7a and 7b comprise one or more binding area(s) 8 on a sensor surface 1, which comprise(s) specific binding molecules. Additionally, the cartridge 7a comprises label particles 2, which are typically provided at the cover of the cartridge 7a. From the cartridge 7a the label particles 2 can be detached, especially by dissolving into a liquid sample. One side of the cartridge 7a, 7b, especially the top or cover of the cartridge 7a, 7b may be a film or a tape. The tape can be adhesive and easily be affixed to the top of the walls of the cartridge 7a, 7b opposite to the bottom of the cartridge 7a, 7b. Providing an adhesive tape also facilitates the attachment of the label particles 2 to the cartridge 1. According to another example of the present invention, these label particles 2 are provided on the sensor surface 1 as shown in FIG. 2b, for example next to the binding area 8. However, it is also possible to provide the label particles 2 on top of the binding area 8.

Several experiments have been performed by the inventors in order to prove the efficacy of the proposed methods. Label particles 2 have been supplied a) next to the binding sites 8 and b) on top of the binding areas 8. This shall be exemplified by the following examples:

EXAMPLE 1

The aim of example 1 was to do assays with the dried beads as close as possible to the printed binding areas 8 (spots) on the sensor surface 1 (substrate).

Materials:
500 nm functional super-paramagnetic bead solution
Drying buffer (consisting of 10% sucrose)
Printed optical substrates: spotted with 4 spots BSA (Bovines Serumalbumin)-drug
Sample liquid (concentrated assay buffer)

Methods:
Preparing the bead solution, i.e. the liquid sample with dissolved labeled particles 2, is done by washing 160 µl bead solution and redispersing the beads in 40 µl drying buffer (up-concentration of 4×). Then, 1 droplet of 75 nl of the bead solution is dosed on the substrate or sensor surface 1. Dosing is done as close as possible to the printed spots of binding area 8. The optical substrate or cartridge 7a, 7b with dosed beads or labeled particles 2 is assembled with a top part and stored over night at room-temperature prior to use.

Measuring:
Experiments are performed by supplying 17 µl of a sample liquid to the assembled cartridge 7a, 7b. Three seconds after supplying the sample liquid to the cartridge 7a, 7b, the beads are redispersed. Acceleration of bead movement is done after this by using magnetic actuation. Detection is performed with a CCD (Charged Coupled Device) setup.

Results:
When the actuation starts, the beads or label particles 2 start binding to the printed spots of binding sites 8 that are closest to the place where the dry label particles 2 were situated. During actuation one can see them binding also more and more to the other spots. Different actuation schemes give different results.

Figure 3A:
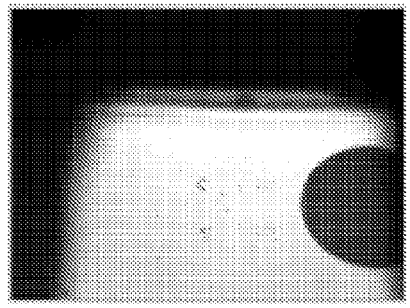
FIG. 3a shows a FTIR image of a sensor surface prior to redispersion.
Figure 3B:
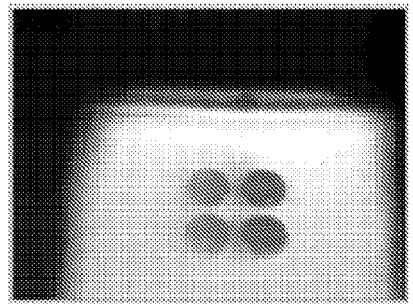
FIG. 3b shows the image of FIG. 3a after redispersion and binding.

The visual results are shown in FIG. 3. FIG. 3a shows the dry functional label particles 2 prior to redispersion in the liquid sample as a large dark spot or circle before a bright background. FIG. 3b at he right shows the label particles 2 after redispersion and binding, bound to the binding areas 8 (printed spots) on the sensor surface 1, which are now visible as four dark circular spots before a bright background. It shall be appreciated that the dry label particles 2 have nearly completely vanished after the redispersion step, i.e. most of the label particles 2 are dissolved in the liquid sample and bound to the binding areas 8 in FIG. 3b. By contrast, after the binding of the label particles 2 to the binding areas 8, a clear signal resulting from these binding areas 8 is visible.

EXAMPLE 2

It was the aim of example 2 to do assays with the dried label particles 2 on top of the printed binding areas 8 (printed spots) on the sensor surface 1 (substrate). For the sake of clarification an assay is also a procedure where a property or concentration of an analyte is measured.

Materials:
500 nm functional super-paramagnetic bead solution
Drying buffer (consisting of 10% sucrose)
Printed optical substrates: spotted with 3 spots BSA-drug
Sample liquid (concentrated assay buffer)

Methods:

Preparing the bead solution is done by washing 160 µl bead solution and redispersing the label particles 2 in 40 µl drying buffer (up-concentration of 4×). Then, 1 droplet of 75 nl of the bead solution, i.e. the liquid sample in which the label particles 2 dissolve, is dosed on the substrate. In this case, dosing is done on the printed spots of the binding areas 8. The optical substrate with dosed label particles 2 is assembled with a top part and stored over night at room-temperature prior to use.

Measuring:

Experiments are performed by supplying 17 µl of a sample liquid to the assembled cartridge 7a, 7b. Three seconds after supplying the sample liquid to the cartridge 7a, 7b, the label particles 2 are redispersed. Acceleration of bead movement is done after this by using magnetic actuation. Detection is performed with a CCD setup.

Results:

After supplying the sample liquid the label particles 2 are redispersed within three seconds. When the actuation starts, the label particles 2 start binding to the three printed spots at the binding area 8. During actuation one can see the spots become darker and darker.

Figure 4A:
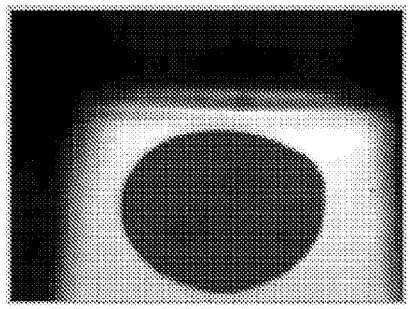
FIG. 4a shows an FTIR image of another sensor surface prior to redispersion.
Figure 4B:
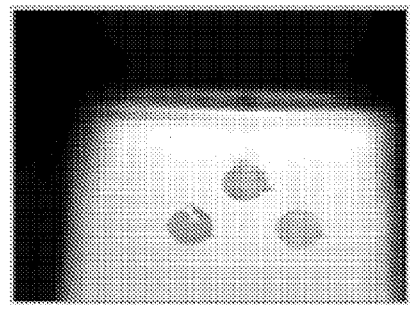
FIG. 4b shows the image of FIG. 4a after redispersion and binding.

The visual results are shown in FIG. 4. FIG. 4a shows the dry functional label particles 2 prior to redispersion as a large dark circular spot. FIG. 4b shows the label particles 2 after redispersion and binding, bound to the binding areas 8 (printed spots) on the sensor surface 1, which are now visible as three gray circular spots before a light background in FIG. 4b.

The invention is described herein with respect to the optical detection method of frustrated total internal reflection (FTIR), this does not exclude the invention to be implemented with different optical detection methods, as the measurement of non-scattered light. The principles discussed here can mutatis mutandis be applied to the detection of photoluminescence, too. It is to be noted that in the case of photoluminescence or direct scattering detection the detector 4a may also be positioned in a direction other than the output light beam 4, e.g. in a direction perpendicular to the sensor surface 1.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A method of detecting the redispersion of dry particles into a solution, the method comprising acts of:
    a) providing a sensor surface with dry particles;
    b) illuminating the sensor surface with light along a first optical path and detecting the light reflected by the sensor surface, wherein the angle between the first optical path and the sensor surface fulfils a condition of total internal reflection;
    c) providing a liquid to a volume in contact with the sensor surface; and
    d) detecting the reflected light while the dry particles redisperse into the liquid.

2. The method according to claim 1, comprising an act of analyzing a total amount of redispersed particles.

3. The method according to claim 1, comprising an act of analyzing a rate of the redispersion of the particles.

4. The method according to claim 1, wherein the dry particles are label particles.

5. The method according to claim 1, wherein the particles are magnetic beads.

6. The method according to claim 1, further comprising an act of aligning at least one of the first optical path and an FTIR detector with respect to the dry particles.

7. The method according to claim 1, wherein the act of providing the sensor surface with the dry particles comprises an act of providing an FTIR cartridge comprising said sensor surface accessible for FTIR detection, said sensor surface comprising at least one binding area, wherein the dry particles are situated on said sensor surface.

8. The method according to claim 7, wherein the label particles are situated on the at least one binding area of said sensor surface.

9. The method according to claim 1, comprising an act of providing an adhesive attaching the dry particles to the sensor surface.

10. The method according to claim 9, wherein the act of providing the adhesive comprises an act of applying an adhesive film to the sensor surface.

11. The method according to claim 9, wherein the act of providing the adhesive comprises an act of applying an adhesive tape to the sensor surface.

\* \* \* \* \*